United States Patent
Luke et al.

(10) Patent No.: US 8,904,501 B2
(45) Date of Patent: Dec. 2, 2014

(54) METHOD AND SYSTEM FOR AUTOMATED EMERGENCY ACCESS TO MEDICAL RECORDS

(75) Inventors: Wallace J. Luke, Pleasanton, CA (US); Tom Eliaz, San Francisco, CA (US); Michael John Kozuch, Pleasanton, CA (US)

(73) Assignee: Rule 90 Technologies, Inc., Pleasanton, CA (US)

( * ) Notice: Subject to any disclaimer, the term of this patent is extended or adjusted under 35 U.S.C. 154(b) by 630 days.

(21) Appl. No.: 12/709,481

(22) Filed: Feb. 21, 2010

(65) Prior Publication Data

US 2011/0209205 A1 Aug. 25, 2011

(51) Int. Cl.
| | | |
|---|---|---|
| G06F 7/04 | (2006.01) | |
| G06F 12/14 | (2006.01) | |
| G06F 17/30 | (2006.01) | |
| H04L 29/06 | (2006.01) | |
| H04L 9/32 | (2006.01) | |
| G06F 21/00 | (2013.01) | |
| G06Q 50/00 | (2012.01) | |
| G06F 19/00 | (2011.01) | |
| G06F 21/62 | (2013.01) | |
| G06Q 50/24 | (2012.01) | |
| G06F 21/31 | (2013.01) | |
| G06Q 50/22 | (2012.01) | |

(52) U.S. Cl.
CPC ........... *G06F 19/322* (2013.01); *H04L 63/0428* (2013.01); *G06F 21/6218* (2013.01); *G06Q 50/24* (2013.01); *G06F 21/6209* (2013.01); *H04L 63/08* (2013.01); *G06F 21/31* (2013.01); *H04L 63/083* (2013.01); *G06Q 50/22* (2013.01); *G06F 19/323* (2013.01)
USPC ........ 726/6; 726/5; 726/22; 726/29; 713/165; 713/168; 713/182; 705/2; 705/3

(58) Field of Classification Search
CPC ... H04L 63/08; H04L 63/083; H04L 63/0428; G06F 21/31; G06F 21/6218; G06F 21/6209; G06F 19/322; G06Q 50/22; G06Q 50/24
USPC .............. 726/6, 5, 22, 29; 713/165, 168, 182; 705/2, 3
See application file for complete search history.

(56) References Cited

U.S. PATENT DOCUMENTS

| | | | |
|---|---|---|---|
| 2003/0074564 A1* | 4/2003 | Peterson | 713/182 |
| 2003/0167269 A1* | 9/2003 | Gupta | 707/9 |
| 2008/0319798 A1* | 12/2008 | Kelley | 705/3 |
| 2009/0007237 A1* | 1/2009 | Lorsch | 726/3 |
| 2009/0055222 A1* | 2/2009 | Lorsch | 705/3 |
| 2009/0160617 A1* | 6/2009 | Mullen et al. | 340/10.1 |
| 2009/0198696 A1* | 8/2009 | Banks | 707/9 |
| 2009/0228352 A1* | 9/2009 | Waxman et al. | 705/14 |
| 2009/0295569 A1* | 12/2009 | Corwin et al. | 340/539.12 |

* cited by examiner

*Primary Examiner* — Aravind Moorthy
(74) *Attorney, Agent, or Firm* — David S Nagy

(57) ABSTRACT

This invention is a method and a system for accessing medical records of an injured party by an emergency responder through a secure website, utilizing a portable emergency access card provided with at least one item of information of the victim, while offering safeguards for the confidentiality of the victim's information and records.

19 Claims, 2 Drawing Sheets

METHOD AND SYSTEM FOR AUTOMATED EMERGENCY ACCESS TO MEDICAL RECORDS

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

This invention relates to medical record accessing systems, and more particularly to a method and a system for accessing medical records of a user by an emergency responder through a secure website utilizing a portable emergency access card provided with at least one information of the user.

DISCUSSION OF RELATED ART

In medical emergencies it is not uncommon for a victim to be incapacitated to the point that they are unable to communicate, due to unconsciousness, with medical first responders. Of immediate concern to emergency medical responders is whether a patient or victim has any pre-existing conditions, allergies, or reactions to medical treatment that may be required.

Numerous doctors have recommended that individuals carry a digital smart card, flash memory stick or some other device which carries all their medical information. These devices could be carried on the person at all times, either in their wallet, pocket or in a purse. However, the drawback to this solution lies in losing these devices either through theft or misplacement, and then all the personal health information or data for that person goes with it. The data may not necessarily be lost, since there is most likely a backup at the source of the data, however with the loss of a device there is a loss of personal privacy. There are other situations, where the devices require the user to enter a password or login code to view the information. While this is an important step in security, when the patient is incapacitated, then the device is rendered useless, since access to the information on the device would be denied.

A solution is required which allows critical information to be made available to early responders in an emergency. Many responders now have internet access through cell phones or mobile devices which facilitates a solution to the problem of accessing information that might not be carried on the victim of the emergency. Our solution capitalizes on the technologies available as well as the typical habits of individuals in how they carry important items on their person such as cash, ID cards, personal care products, etc. Only by understanding these behaviors can a reasonable solution be designed that ensures effective outcomes in the event of an emergency. Therefore, there is a need for a method and a system for accessing medical records of a user by an emergency responder through a secure site, such as a website, having a private area and an emergency access area wherein the information stored in the private area can be copied into the emergency access area through an emergency access manager module. Further, such a system would include a wallet-sized portable emergency access card that is created by triggering an automatic access number generator which provides at least one information that allows the user and/or emergency responder to access the emergency access area on the website. Such an emergency access card would be printed and easily carried by the user so as to facilitate access to the emergency access area by the emergency responder. Moreover, such a system would include more options for the emergency responder to access the emergency access area using the information printed on the emergency access card. The present invention accomplishes these objectives.

SUMMARY OF THE INVENTION

The present invention is a method and a system for retrieving medical records of at least one user by an emergency responder through a secure website. The secure site, such as a website, comprises a private area having at least one information and the medical records, which are a collection of medical information, data, images or drawings of the at least one user. The site can be accessed by entering a username and a password. The private area further includes an emergency access manager module rendered with an emergency access card and a button-activated interface. The at least one information and the medical records are available at the user's discretion through an emergency access manager module, that may facilitate the at least one user to copy the at least one information from the private area into an emergency access area that may be "read only". The at least one information may be security information such as a website with a unique code or number, photograph, voice, biometric identifier or other personal details of the at least one user.

The user can register into the secure website by entering at least one information and log in to the website by entering a username and a password. The emergency access manager module facilitates the user to upload and store at least one information to the private area through the emergency access manager module. The user can choose at least one protocol and at least one platform to deliver the at least one information to the emergency access area through the emergency access manager module. The at least one protocol may be selected from a group consisting of MMS, SMS and email. The at least one platform may be selected from a group consisting of website (HTML), PDF report and voice recording.

The button activated interface may be activated by a mouse-click for triggering the automatic access number generator to compute a random number, unique bar code, or a unique image of the at least one user which displays another web page that contains a wallet-sized image of the emergency access card. The emergency access card provides at least one information that allows the user to access the emergency access area. The card can be printed and carried by the user so as to facilitate access to the emergency access area by the emergency responder.

Initially, the emergency responder may search for the emergency access card that includes the at least one information and the medical records to access the emergency access area. The emergency access area can be accessed by entering the at least one information through at least one mode of operation. The at least one mode of operation may be entering into a secure website with a unique code or number indicated on the emergency access card utilizing a mobile device of the emergency responder.

The at least one mode of operation may be taking at least one photograph of a bar code and/or unique identifier suggested on the emergency access card with a camera phone and sending the photograph using at least one protocol and at least one platform to an electronic address or number indicated on the emergency card. The at least one mode of operation may be taking a photograph of any number of cards such as insurance card, driver's license, PAN card or other identification mentioned on the emergency access card and sending the photograph using at least one protocol and at least one platform to an electronic address or number indicated on the emergency card. The at least one mode of operation may also be using a biometric identifier, such as fingerprints, retinal scans or tattoos, indicated on the emergency access card to access the emergency access area. The at least one information may be sent to a server through the at least one mode of operation, wherein the server includes a recognition program that deciphers the at least one information and matches it to the emergency access area.

DESCRIPTION OF THE DRAWINGS

A more complete appreciation of the invention will be readily obtained by reference to the following detailed description when considered in connection with the accompanying drawings, wherein.

DETAILED DESCRIPTION OF THE PREFERRED EMBODIMENT

Figure 1:
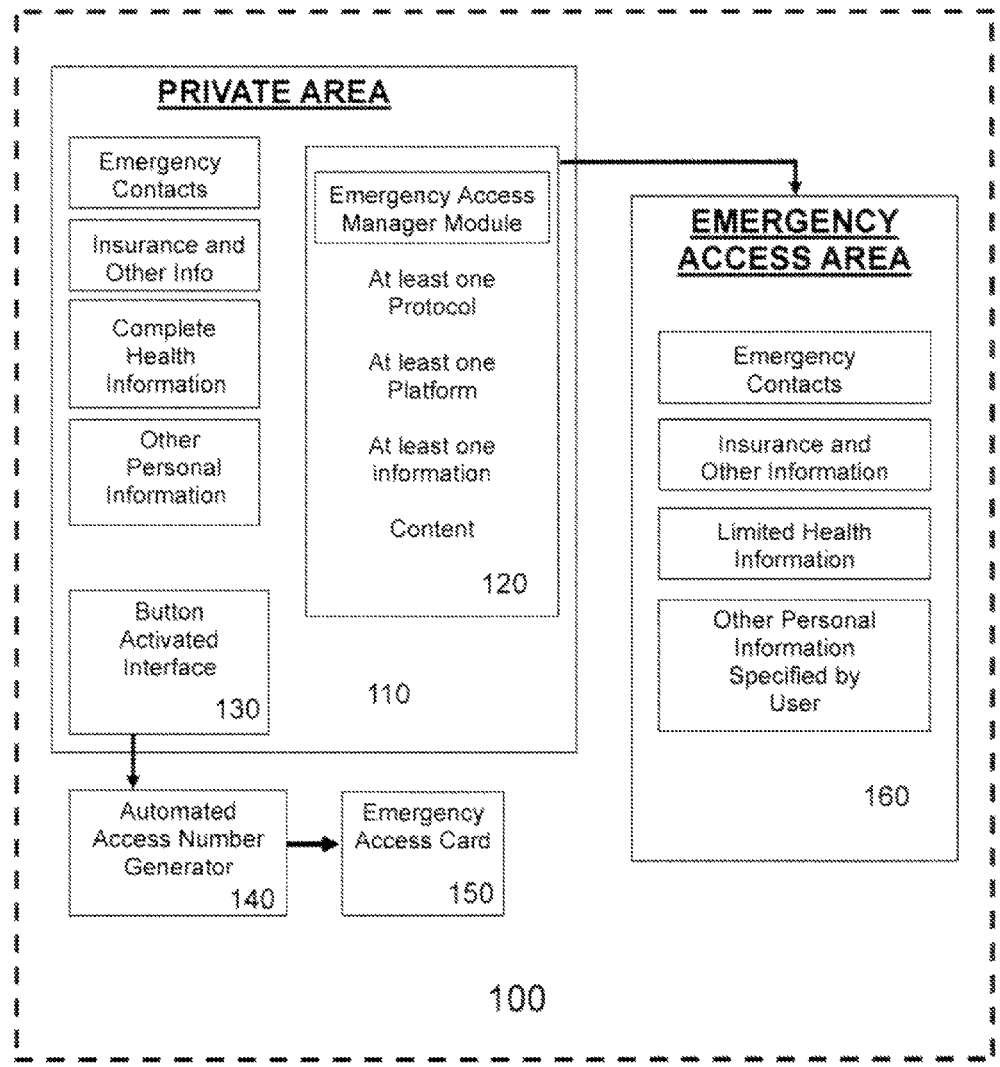
FIG. 1 is a high level flow diagram of the management functionality of the emergency access area and codes according to an embodiment of the present invention.
Figure 2:
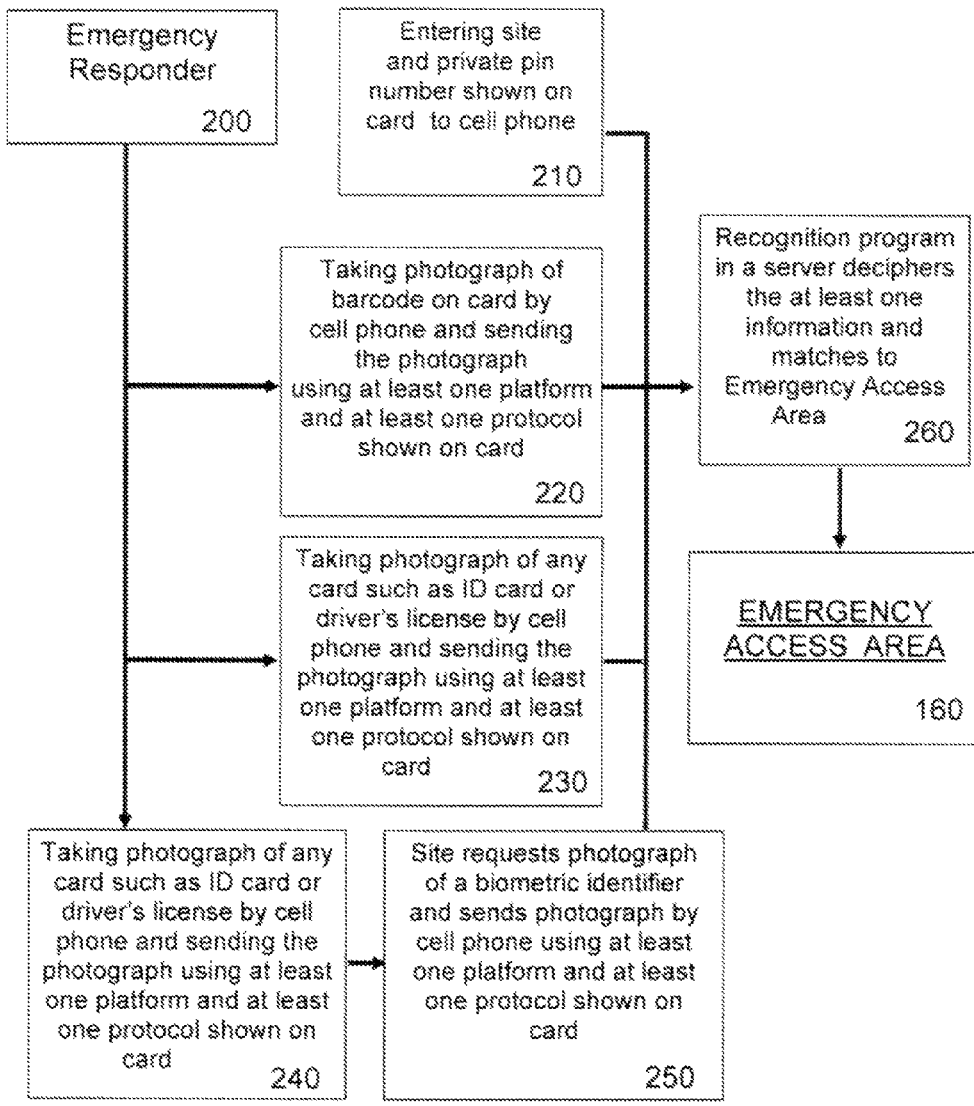
FIG. 2 is a flow diagram of the general access to the emergency access area according to an embodiment of the present invention.

Referring to the drawings, a preferred embodiment illustrates a method and a system for retrieving medical records of at least one user by an emergency responder (not shown) through a secure site 100 and generally indicated in FIGS. 1 and 2. The secure site 100 comprises a private area 110 having at least one information and medical records, which is a collection of medical information, data, images and/or drawings of the at least one user. The site 100 can be accessed by entering a username and a password. The private area 110 further includes an emergency access manager module 120 rendered with an emergency access card 150 and a button-activated interface 130.

The at least one information and the medical records are available at the user's discretion through an emergency access manager module 120, that may facilitate the at least one user to copy the at least one information from the private area 110 into an emergency access area 160 that may be "read only". The at least one information may be security information such as a website with a unique code or number, photograph, voice, biometric identifier or other personal details of the at least one user. The user can register into the secure website 100 by entering at least one information and log in to the website 100 by entering a username and a password.

The emergency access manager module 120 facilitates the user to upload and store at least one information to the private area 110 through the emergency access module 120. The user can choose at least one protocol and at least one platform to deliver the at least one information to the emergency access area 160 through the emergency access manager module 120. The at least one protocol may include multimedia messaging service (MMS), short message service (SMS), and email. The at least one platform may be include website (HTML), PDF report and voice recording.

The button-activated interface 130 may be activated by a mouse-click for triggering the automatic access number generator 140 to compute a random number, unique bar code, or a unique image of the at least one user which displays another web page or a PDF file that contains a wallet-sized image of the emergency access card 150. The emergency access card 150 provides at least one information that allows the user to access the emergency access area 160. The card 150 can be printed and carried by the user so as to allow the emergency responder (not shown) to gain access to the emergency access area 160. The emergency access card 150 provides instructions to the user on how to access the emergency access area 160 or repository of the medical information by providing the required at least one information that was created through the emergency access manager module 120. The at least one information may be available as is or with modification, for example a social security number may be truncated to show only the last 4 digits, or an address may be reduced to only a zip code.

FIG. 2 illustrates a flow diagram of access to the emergency access area 160 of the at least one user by an emergency responder 200. Initially, the emergency responder 200 may search for the emergency access card 150 that includes the at least one information to access the emergency access area 160. The emergency access area 160 can be accessed by entering the at least one information through at least one mode of operation. The at least one mode of operation 210 may be entering into the secure website 100 with a unique code or number indicated on the emergency access card 150 utilizing a mobile device of the emergency responder 200. The code may be sent to a server that includes a recognition program 260 that deciphers the code and matches it to the emergency access area 160.

The at least one mode of operation (220 or 230) may be taking one or more photographs of a bar code and/or unique identifier, and/or any number of cards such as insurance card, driver's license, PAN card, etc., mentioned on the emergency access card 150, with a camera phone and sending the photograph using at least one protocol and at least one platform, as previously described, to an electronic address or number indicated on the emergency access card 150. The photograph(s) may sent to the server that includes a recognition program 260 that deciphers unique numbers or bar codes from the photographs and matches these numbers to the emergency access area 160 that contains the authorized information.

As a further variation 240, the server may request a second form of identification, which may be a photograph of a biometric identifier such as fingerprints, retinal scans or tattoos 250, as indicated on the emergency access card 150, to access the emergency access area 160. In this variation, the server will include a recognition program that can recognize and identify such biometric identifiers.

The present invention may suitably comprise, consist of, or consist essentially of, any element of the various parts or features of the invention, and their equivalents as described herein. Further, the present invention illustratively disclosed herein may be practiced in the absence of any element, whether or not specifically disclosed herein. Numerous modifications and variations of the present invention are possible in light of the above teachings. It is therefore to be understood that within the scope of the appended claims, the invention may be practiced otherwise than as specifically described herein.

Plainly, this invention is applicable to the access of private medical records. While this invention was conceived to address pressing needs in the medical field, it can be seen that it is readily adaptable to other arenas in which entities require limited or full access to any such online record, application, document or image. Thus, while the descriptions herein have focused on medical applications, they can all be seen to have their analogs in other applications and fields of endeavor.

What is claimed is:

1. A system for retrieving records of at least one user by an emergency responder through a secure site, the system comprising:
   a mobile phone or other device capable of accessing the site;
   an emergency access manager module;
   a private area on the site having at least one information regarding the at least one user, uploaded and stored through the emergency access module;
   the choice by the at least one user of at least one protocol and at least one platform to deliver the at least one information to an emergency access area through the emergency access manager module
   a button activated interface wherein the button activated interface triggers an automatic access number generator for displaying a web page with an emergency access card; and
   the emergency access area on the site being defined as read only, containing limited records of the sort needed by emergency responders selected from the private area by the user and which can be accessed by entering the at least one information indicated on the emergency access card.

2. The system of claim 1 wherein the records may be a collection of medical information, data, or images of the at least one user.

3. The system of claim 1 wherein the emergency access manager module may facilitate the at least one user to copy at least one information into the emergency access area from the private area.

4. The system of claim 1 wherein the at least one information may include security information such as a website with a unique code, unique number, photograph, voice recording, biometric identifier, or other personal details of the at least one user.

5. A method for retrieving records of at least one user by an emergency responder through a secure site, the method comprising the steps of:
   (a) registering the at least one user into the secure site by entering at least one information;
   (b) logging into the secure site by entering a username and a password;
   (c) creating a private area on the site with an emergency access manager module;
   (d) creating a read-only emergency access area on the site which contains limited records of the sort needed by emergency responders responders selected from the private area by the user, to which entry may be effected with an emergency access card through the emergency access manager module;
   (e) facilitating the ability for the at least one user to upload and store the at least one information to the private area through the emergency access manager module;
   (f) facilitating the ability for the at least one user to choose at least one protocol, and at least one platform to deliver the at least one information to the emergency access area through the emergency access manager module;
   (g) clicking on the button activated interface for triggering the automatic access number generator; and
   (h) accessing the emergency access area using the emergency access card, which card does not provide access to the private area.

6. The method of claim 5 wherein the records may be a collection of medical information, data, images, and/or drawings of the at least one user.

7. The method of claim 5 wherein the emergency access manager module may facilitate the at least one user to copy at least one information into the emergency access area from the private area.

8. The method of claim 5, wherein the step of creating an emergency access area rendered with an emergency access card comprises:
   (a) accessing the site by entering the username and the password;
   (b) displaying a web page with the emergency access card; and
   (c) printing the emergency access card and having it carried by the at least one user so as to gain access to the emergency access area by the emergency responder.

9. The method of claim 8 wherein the emergency access card provides the at least one information to access the emergency access.

10. The method of claim 8 wherein the at least one information may be security information such as a website with a unique code, unique number, photograph, voice recording, biometric identifier, or other personal details of the at least one user.

11. The method of claim 8 wherein the automatic access number generator is triggered to compute a random number, a unique bar code, or a unique image of the at least one user.

12. The method of claim 8 wherein the at least one protocol may be selected from a group consisting of multimedia messaging service (MMS), short message service (SMS) and email.

13. The method of claim 8 wherein the at least one platform may be selected from a group consisting of website (HTML), PDF report and voice recording.

14. The method of claim 5, wherein the step of accessing the emergency access area using the emergency access card by the emergency responder comprises:
   (a) providing or finding the emergency access card that includes at least one information to access the emergency access area; and
   (b) accessing the emergency access area by entering at least one information through at least one mode of operation.

15. The method of claim 14 wherein the at least one information may be sent to a server through the at least one mode of operation, wherein the server includes a recognition program that deciphers the at least one information and matches it to the emergency access area.

16. The method of claim 14 wherein the at least one mode of operation may be entering into a website with a unique code or unique number indicated on the emergency access card, utilizing a mobile device of the emergency responder.

17. The method of claim 14 wherein the at least one mode of operation may be taking a photograph of a bar code and/or a unique identifier suggested on the emergency access card with a camera phone of the emergency responder and sending the photograph using at least one protocol and at least one platform to an electronic address or number indicated on the emergency access card.

18. The method of claim 14 wherein the at least one mode of operation may be taking a photograph of any number of cards such as driver's license, insurance card, PAN card or other identification mentioned on the emergency access card and sending the photograph using at least one protocol and at least one platform to an electronic address or number indicated on the emergency access card.

19. The method of claim 14 wherein the at least one mode of operation may be using a biometric identifier, such as finger prints, retinal scan or tattoos, indicated on the emergency access card, to access the emergency access area.

\* \* \* \* \*